(12) United States Patent
Jorneus et al.

(10) Patent No.: US 10,231,804 B2
(45) Date of Patent: Mar. 19, 2019

(54) IMPLANT ARRANGEMENT WITH AN INTERNAL SOCKET FOR A TURNING TOOL

(71) Applicant: NOBEL BIOCARE SERVICES AG, Kloten (CH)

(72) Inventors: Lars Jorneus, Frillesås (SE); Sanel Duric, Gothenburg (SE)

(73) Assignee: NOBEL BIOCARE SERVICES AG, Kloten (CH)

(*) Notice: Subject to any disclaimer, the term of this patent is extended or adjusted under 35 U.S.C. 154(b) by 0 days.

(21) Appl. No.: 14/973,509

(22) Filed: Dec. 17, 2015

(65) Prior Publication Data

US 2016/0100916 A1 Apr. 14, 2016

Related U.S. Application Data

(60) Division of application No. 13/428,772, filed on Mar. 23, 2012, now abandoned, which is a continuation of
(Continued)

(30) Foreign Application Priority Data

Oct. 1, 2003 (SE) .................................... 0302597-0

(51) Int. Cl.
- *A61C 8/00* (2006.01)
- *A61B 17/88* (2006.01)
- *A61B 17/86* (2006.01)

(52) U.S. Cl.
CPC ........ *A61C 8/0037* (2013.01); *A61B 17/8877* (2013.01); *A61C 8/0018* (2013.01);
(Continued)

(58) Field of Classification Search
CPC ....... A61C 8/00; A61C 8/0013; A61C 8/0089; A61C 8/009
(Continued)

(56) References Cited

U.S. PATENT DOCUMENTS

| | | | | | |
|---|---|---|---|---|---|
| 4,089,357 A | * | 5/1978 | Gill | ..................... | F16B 23/0023 411/404 |
| 4,464,957 A | * | 8/1984 | Gill | ..................... | F16B 23/0023 81/460 |

(Continued)

FOREIGN PATENT DOCUMENTS

| | | |
|---|---|---|
| EP | 0696445 A1 | 2/1996 |
| EP | 1481646 | 12/2004 |

OTHER PUBLICATIONS

Decision to Grant in EP Appl. No. 04775473.4 dated Apr. 5, 2013, in 2 pages.
(Continued)

*Primary Examiner* — Yogesh Patel

(74) *Attorney, Agent, or Firm* — Knobbe Martens Olson & Bear LLP

(57) ABSTRACT

An implant is provided with an upper portion in which an internal socket extends. The implant can be tightened by a turning instrument which has first lateral surfaces that can cooperate with corresponding second lateral surfaces in the internal socket. One or more of the first and/or second lateral surfaces is/are arranged completely or partially with friction-enhancing means. The implant and the tool are arranged with interacting parts which extend beyond the first and second lateral surfaces and completely or substantially take up bending moments which act in or on said portion or are directed toward said portion and occur in the event of skewing, or a tendency toward skewing, between the implant and the tool. The arrangement counteracts mechanical stresses in said portion, the latter being able to retain its original shape even in the case of implants with small dimensions.

6 Claims, 2 Drawing Sheets

Related U.S. Application Data application No. 10/574,313, filed as application No. PCT/SE2004/001372 on Sep. 24, 2004, now abandoned.

(52) U.S. Cl.
CPC ........ *A61C 8/0089* (2013.01); *A61B 17/8615* (2013.01); *A61C 8/0087* (2013.01); *A61C 2008/0046* (2013.01)

(58) Field of Classification Search
USPC .................................................. 411/402–408
See application file for complete search history.

(56) References Cited

U.S. PATENT DOCUMENTS

| | | | |
|---|---|---|---|
| 4,681,541 A * | 7/1987 | Snaper | A61C 3/02 408/144 |
| 4,960,381 A | 10/1990 | Niznick | |
| 5,019,080 A | 5/1991 | Hemer | |
| 5,061,181 A | 10/1991 | Niznick | |
| 5,105,690 A | 4/1992 | Lazzara et al. | |
| 5,232,361 A | 8/1993 | Sachdeva et al. | |
| 5,246,369 A | 9/1993 | Poulmaire | |
| 5,257,558 A | 11/1993 | Farzin-Nia et al. | |
| 5,259,280 A | 11/1993 | Hoy | |
| 5,279,190 A * | 1/1994 | Goss | B25B 13/065 411/403 |
| 6,016,727 A | 1/2000 | Morgan | |
| 6,132,215 A | 10/2000 | Parsed et al. | |
| 6,394,806 B1 | 5/2002 | Kumar | |
| 6,419,489 B1 | 7/2002 | Jorneus et al. | |
| 6,685,412 B2 | 2/2004 | Altarac et al. | |
| 2002/0177105 A1 | 11/2002 | Engman | |
| 2004/0101807 A1* | 5/2004 | Porter | A61C 8/0001 433/173 |
| 2010/0184002 A1 | 7/2010 | Renck et al. | |
| 2010/0209877 A1 | 8/2010 | Hogan et al. | |

OTHER PUBLICATIONS

International Search Report for Application No. PCT/SE2004/001372.

Patent Board Decision in U.S. Appl. No. 10/574,313 dated Jan. 26, 2012, in 10 pages.

* cited by examiner

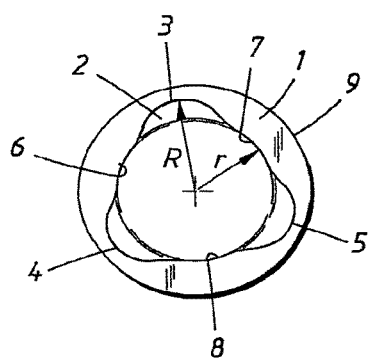
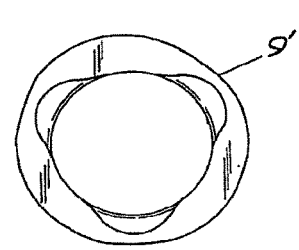
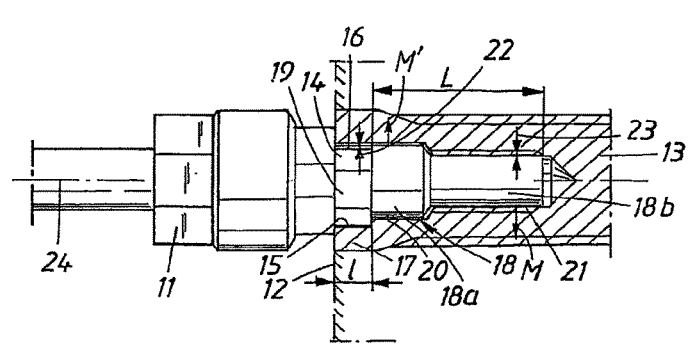

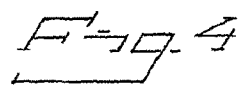
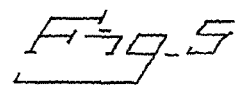
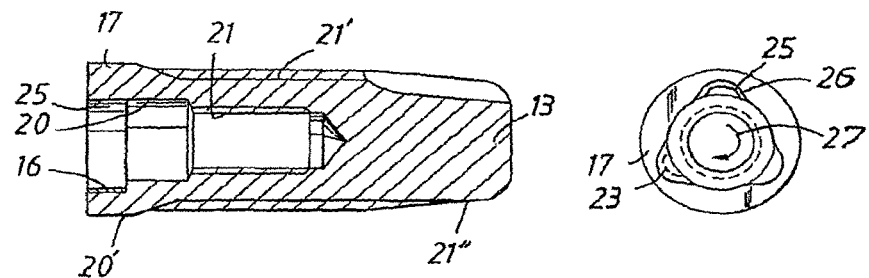
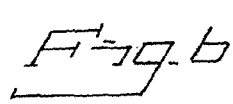
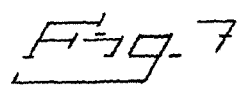
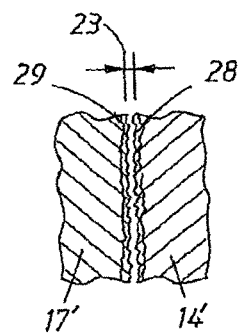
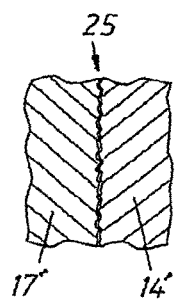

IMPLANT ARRANGEMENT WITH AN INTERNAL SOCKET FOR A TURNING TOOL

CROSS-REFERENCE TO RELATED APPLICATIONS

This application is a divisional of U.S. patent application Ser. No. 13/428,772, filed on Mar. 23, 2012, which is a continuation of U.S. patent application Ser. No. 10/574,313, filed on Dec. 13, 2006, which is the U.S. National Phase of International Application No. PCT/SE2004/001372, filed Sep. 24, 2004, which claims the benefit of Swedish Application No. SE 0302597-0, filed Oct. 1, 2003, the entire contents of these application are hereby incorporated by reference in their entirety.

BACKGROUND OF THE INVENTION

Field of the Invention

The present invention relates to an arrangement for counteracting stress in a portion of an implant provided with an internal socket extending in said portion, via which the implant can be tightened by means of a turning tool or turning instrument which has first lateral surfaces that can cooperate with corresponding second lateral surfaces in the internal socket.

Description of the Related Art

It is already known to anchor implants in holes in the jaw bone with the aid of instruments or tools. The implant can be fitted in a threaded hole or can be of the self-tapping type. It can be screwed in using said internal socket for the tool, and the present invention relates to this type of implant. Reference is here made in quite general terms to implants and methods which are generally known in dentistry in connection with screwing-in of implants.

An implant with an internal socket affords advantages, such as easier connection of spacer elements and other components to the implant. The necessary implantation force/turning force can, however, be relatively high, and the material thickness of the implant is often low, especially in the case where the implant is of small dimensions. This can result in the implant being deformed or being at risk of breaking at the site where the turning force is applied. One reason for this happening is that the internal socket, which has a non-round geometry, is often a polygon or some other geometrical figure that results in outwardly directed forces when the implant is being turned into its position. This results in stresses in the implant which act outward and which force the material out and apart. The most obvious way of improving this situation would be to change the non-round geometry so that the outwardly directed forces were reduced. However, this can often be difficult to do in practice, for production technology reasons among others. In established implant systems, these geometries are already defined, and a large range of known ancillary components are based on these geometries. Changing the geometry would therefore be associated with considerable costs and would cause great technical problems. The invention aims, inter alia, to solve these problems.

Another type of load which can occur on a portion with said socket is a bending load, and this can occur either as the sole problem or as a problem in combination with the disadvantages of the turning forces. If one wishes to change the direction of the implant during implantation thereof, or if the angled handpiece or wrench is not applied properly to the tool/implant, a bending force is exerted which will deflect the implant and which, in addition to producing undesired deformation, can also lead to fracturing of the implant portion/flange which has the socket. The invention also aims to solve this problem.

SUMMARY OF THE INVENTION

The feature which can principally be regarded as characterizing a first combination part of the invention is that one or more of the first and/or second lateral surfaces is/are completely or partially arranged with friction-enhancing means. A second combination part, which can function independently or in combination with the first combination part, can principally be regarded as being characterized in that the implant and the tool are arranged with interacting parts which extend inside the implant and beyond the first and second lateral surfaces and substantially take up bending moments which act in or on said portion or are directed toward said portion and occur in the event of skewing, or a tendency toward skewing, between the implant and the tool.

In further developments of the inventive concept, the means can comprise or consist of a friction-enhancing coating on the first and second surface or surfaces of the tool and implant, respectively. In one embodiment, the means can consist of a chosen degree of roughness on the lateral surface or surfaces concerned. In a second embodiment, the means can consist of the fact that parts of the implant and of the tool which interact during turning are designed to bring about increased friction, which is thus achieved by suitable choice of material for the respective parts of the implant and of the tool/instrument. In a further embodiment, the means can consist of or comprise metal nitrides and/or metal carbides, e.g. titanium nitride, chromium carbide or diamond particles, etc., applied to the surface or surfaces concerned. In a further embodiment, the interaction between the first and second lateral surfaces can be designed to take place only when a degree of loading on the implant and the tool is reached. In one embodiment, the arrangement can also be characterized in that the stress in the implant portion in question can be reduced by up to ca. 30% when titanium nitride is applied.

That part of the tool extending beyond said first surfaces can be ca. 3 to 5 times longer than the longitudinal extents of the first surfaces. Said part extending past can have first and second longitudinally extending parts with different diameters, the first longitudinally extending parts situated next to the first lateral surfaces having the greater diameter. In the event of skewing tendencies or skewing between the implant and the tool, a bending moment occurs which places a load on, inter alia, surface areas of the implant located at the first longitudinally extending part's area nearest to the first lateral surfaces and the outermost part of the second longitudinally extending part. The bending moment is prevented from acting on the portion with the internal socket by virtue of the fact that a slight clearance is initially present between the first and second lateral surfaces. Threads on the implant can also contribute to taking up said bending moments.

By means of what has been proposed above, the stresses acting on the implant flange or portion with the internal socket can be greatly reduced. The advantages of the internal socket on the implant can be retained, and good stability characteristics can be obtained even for implants of small dimensions. The various friction-enhancing means proposed can be combined and/or optimized according to the respective application so as to achieve higher coefficients of friction. The guide pin on the instrument or tool can be considerably lengthened and it will be appreciated, for example, that if the effective length of the pin is doubled, for example, the force in the flange portion reduces by half on account of the fact that the pin can exploit the resistance it meets in the implant.

BRIEF DESCRIPTION OF THE DRAWINGS

A presently proposed embodiment of an arrangement with the characteristics of the invention is described below with reference to the attached drawings, in which:

FIG. 1 is an end view showing the end surface of a portion or a flange which, in an implant, is provided with an internal socket, FIG. 2 is an end view showing the flange/portion according to FIG. 1, but where said flange/portion has been exposed to an outwardly acting force associated with a turning tool or turning instrument (not shown), this outward movement also having caused a deformation of the circumference of the flange/portion, FIG. 3 is a longitudinal view showing a tool applied to an implant (part of which is shown) which has been anchored in a jaw bone (part of which is shown), FIG. 4 is a longitudinal section showing the construction of an implant in question, FIG. 5 is an end view of the implant according to FIG. 4, FIG. 6 is a vertical view showing first and second lateral surfaces coated with friction-enhancing means, when the tool is in a state in which it is not turned in relation to the implant, and FIG. 7 shows a vertical view during interaction with intermediate means, when the tool is turned relative to the implant.

DETAILED DESCRIPTION OF THE PREFERRED EMBODIMENTS

In FIG. 1, a portion of an implant is indicated by 1. The portion constitutes an upper or outer part of the implant and comprises an internal socket 2 for a tool or instrument, described below. In the view shown, the wall of the socket has a polygonal shape with three bulges 3, 4 and 5 and, extending between these, wall parts 6, 7 and 8 with smaller radii. The radii of the bulges 3, 4, 5 are represented by R, and the radii of the wall parts 6, 7 and 8 are represented by r. The circumference is indicated by 9.

FIG. 2 shows an example of how material is forced outward in the already known case. The forcing out or bursting action has caused the circumference 9' to lose its circular shape 9 according to FIG. 1. It will be appreciated that this forcing-out or bursting-out of the material is of great disadvantage for the fixture which is to be applied to the implant. It can, for example, result in accumulation of bacteria, loss of tolerance, etc., in respect of the future fixture.

FIG. 3 shows a turning instrument or turning tool 11 applied to an implant 13 which is or can be anchored in a jaw bone 12. In accordance with the invention, the tool has first lateral surfaces 14 which can cooperate with second lateral surfaces 15 on the implant. In cross section, i.e. at right angles to the plane of the figure according to FIG. 3, the configuration of the first lateral surfaces can correspond to that of the inner walls 3-B in FIG. 1. The second lateral surfaces of the implant can have the configurations shown by 3-8 in FIG. 1. Means 16 on said first and second lateral surfaces are also indicated symbolically in FIG. 3. The means 16 will be arranged to give the turning instrument or turning tool a higher coefficient of friction compared to the case when no such means 16 is present. The flange or portion bearing the internal socket of the implant is indicated by 17 in FIG. 3. The flange or portion has a length 1. The tool 11 is provided with a prolonged guide pin 18 which is made up of two guide pin parts 18a and 18b of different diameters. The guide pin part 18a of greater diameter is situated nearest to the drive part of the tool indicated by 19. The turning tool or turning instrument 11 is of a type which in principle is known per se and it will therefore not be described in detail here. Reference may be made generally to the tool or instrument of the type disclosed in Swedish patent 98/03849-0. The guide pin has a length L which is 3 to 5 times longer than the length 1 of the drive part. The implant is provided with internal recesses 20 and 21 for said guide pin parts 18a and 18b, which are arranged with unthreaded outer surfaces. In the position shown in FIG. 3, the guide pin has a slight clearance 22 in relation to the opposing inner wall of the implant, which inner wall can be threaded. In addition, there is a clearance 23 between the drive part 14 of the tool and the opposing inner wall of the implant. Said clearance 23 is initially present when the tool or instrument is in a state in which it is not turned in relation to the implant. Said clearances 22, 23 are also chosen such that bending moments can be taken up by the guide pin parts 18a and 18b when the tool 11 is skewed or has a tendency to skew relative to the implant, i.e. when the longitudinal axis 24 of the tool is angled in relation to the corresponding longitudinal axis of the implant. Said bending moments are symbolized by M, M'. The clearance is then to be such that the guide pin by itself takes up most of the bending moment, and the drive part 14 is largely prevented from pressing the flange or portion 17 radially outward, compared to the case according to FIG. 2.

FIG. 4 shows, inter alia, the internal surfaces 20 and 21 of the implant which constitute guide surfaces for the tool parts 18a and 18b in FIG. 3. The figure also shows the means 16 arranged in connection with the second inner surfaces (indicated symbolically by 25) of the flange or portion 17 of the implant. The recess 21 is threaded in order to participate in a securing function for an implant screw (not shown) used for fitting a dental replacement part on the implant.

FIG. 5 shows, inter alia, the clearance 23 between the first and second lateral surfaces of the tool and implant, respectively. Said clearance is present when the tool is in a position not turned relative to the implant. This clearance means that, in the event of the bending moments discussed above, the tool is largely prevented from pressing the material of the flange or portion 17 outward in the radial direction. Reference number 25 designates the contact between parts of the first lateral surfaces and corresponding parts of the second lateral surfaces 26. It will be appreciated that the turning interaction takes place only at the parts concerned. In the present case, the direction of turning is clockwise, as has been indicated by the arrow 27.

FIG. 6 shows the case where the opposing first and second lateral surfaces 14' and 17' are in the state in which the turning tool is not turned relative to the implant. The clearance 23 is present between the surfaces. A first means 28 is arranged on the first lateral surface of the tool, and a second means 29 is arranged on the second lateral surface of the flange or portion. These means can in principle be the same means or consist of different means. Alternatively, only one of the first and second lateral surfaces can be provided with said means. In accordance with the above, the means can consist of a chosen surface roughness, metal nitrides and/or metal carbides, such as titanium nitride or chromium carbide, or a mixture of these means, diamond particles, different material selections, etc., see above. In FIG. 4, the internal thread on the implant 12 is indicated by 21'. A surface area of the implant 12 which participates in taking up the bending moment M is indicated by 21", and a surface area which takes up the bending moment M' is indicated by 20'.

FIG. 7 shows the case where the opposing first and second lateral surfaces 14' and 17' cooperate with one another via the intermediate means, i.e. when the turning tool is turned in relation to the implant. The contact between the surfaces is indicated symbolically by 25.

The invention is not limited to the above embodiment given by way of example, and instead it can be modified within the scope of the attached patent claims and the inventive concept.

What is claimed is:

1. A method of driving a dental implant into a supporting structure comprising:
   advancing a turning instrument into an internal recess of the implant such that a first lateral surface of the turning instrument aligns longitudinally with a second lateral surface of the implant, the first lateral surface comprising a surface treatment that enhances the coefficient of friction of the first lateral surface, the turning instrument having a guide pin extending distally beyond the first lateral surface, the turning instrument being sized so that a clearance exists between the guide pin and the internal recess when the turning instrument is advanced into the internal recess, the clearance being adapted so that the guide pin by itself takes up most of a bending moment that occurs due to a longitudinal axis of the turning instrument being angled in relation to a longitudinal axis of the internal recess; and
   rotating the turning instrument to bring the first lateral surface into contact with the second lateral surface, thereby transmitting a torque to the implant and driving the dental implant into the supporting structure.

2. The method of claim 1, wherein the surface treatment comprises a material selected from the group consisting of metal nitrides, metal carbides, and diamond particles.

3. The method of claim 1, wherein the surface treatment enhances a surface roughness of the first lateral surface.

4. The method of claim 1, further comprising:
   skewing the turning instrument so that a longitudinal axis of the turning instrument is angled relative to a longitudinal axis of the implant; and
   engaging an inner surface of the implant with the guide pin of the turning instrument.

5. The method of claim 4, wherein the guide pin is configured to take up a first bending moment that is greater than a second bending moment imparted on the first lateral surface of the turning instrument.

6. The method of claim 4, wherein the guide pin extends distally beyond the first lateral surface by a distance that is 3 to 5 times a longitudinal length of the first lateral surface.

* * * * *